(12) United States Patent
Lucero et al.

(10) Patent No.: US 8,048,933 B2
(45) Date of Patent: Nov. 1, 2011

(54) PROCESS AND CATALYST FOR PRODUCTION OF MIXED ALCOHOLS FROM SYNTHESIS GAS

(75) Inventors: Andrew J. Lucero, Laramie, WY (US); Vijay K. Sethi, Laramie, WY (US); William H. Tuminello, Laramie, WY (US)

(73) Assignee: University of Wyoming Research Corporation, Laramie, WY (US)

( * ) Notice: Subject to any disclaimer, the term of this patent is extended or adjusted under 35 U.S.C. 154(b) by 312 days.

(21) Appl. No.: 12/298,733

(22) PCT Filed: Apr. 27, 2007

(86) PCT No.: PCT/US2007/010342
§ 371 (c)(1),
(2), (4) Date: Oct. 27, 2008

(87) PCT Pub. No.: WO2007/127429
PCT Pub. Date: Nov. 8, 2007

(65) Prior Publication Data
US 2010/0317750 A1    Dec. 16, 2010

Related U.S. Application Data

(60) Provisional application No. 60/796,068, filed on Apr. 27, 2006.

(51) Int. Cl.
*C07C 27/00* (2006.01)
(52) U.S. Cl. ......... 518/717; 518/714; 518/715; 518/700
(58) Field of Classification Search ................... 518/700, 518/714, 715, 717
See application file for complete search history.

(56) References Cited

U.S. PATENT DOCUMENTS

| | | |
|---|---|---|
| 4,151,190 A | 4/1979 | Murchison et al. |
| 4,544,674 A | 10/1985 | Fiato et al. |
| 4,547,601 A | 10/1985 | Holland et al. |
| 4,568,449 A | 2/1986 | Angmorter et al. |
| 4,749,724 A | 6/1988 | Quarderer et al. |
| 4,752,623 A | 6/1988 | Stevens et al. |
| 4,831,060 A | 5/1989 | Stevens et al. |
| 4,882,360 A | 11/1989 | Stevens |
| 5,080,872 A | 1/1992 | Jezel et al. |
| 5,277,794 A | 1/1994 | Delaney et al. |
| 5,308,597 A | 5/1994 | Ledoux et al. |
| 5,345,019 A | 9/1994 | Bigeard et al. |
| 5,391,524 A | 2/1995 | Ledoux et al. |
| 6,060,524 A | 5/2000 | Casanave et al. |
| 6,100,304 A | 8/2000 | Singleton et al. |
| 6,368,997 B2 | 4/2002 | Herron et al. |
| 6,369,286 B1 | 4/2002 | O'Rear |
| 6,491,880 B1 | 12/2002 | Wang et al. |
| 6,638,889 B1 | 10/2003 | Van Berge et al. |
| 6,706,661 B1 | 3/2004 | Kryiova et al. |

OTHER PUBLICATIONS

Xiang et al., nickel and potassium promoted molybdenum carbide for mixed alcohols synthesis via syngas (preprints of symposia—American Chemical Society, Division of fuel Chemistry (2006), 51 (2), 851-852.*

Anderson, R.B.; "Synthesis of Alcohols by Hydrogenation of Carbon Monoxide," Industrial and Engineering Chemistry, vol. 44, No. 10, p. 2418.

Anderson, R.B.; "Nitrided Iron Catalysts for the Fischer-Tropsch Synthesis in the Eighties," Catalysis Review, Sci. Eng., 1980, 21(1), pp. 53-71.

Woo, H.C; Park, K.Y; Kim, Y.G.; Nam, I; Chung, J.S.; Lee, J.S.; "Mixed alcohol synthesis from carbon monoxide and dihydrogen over potassium-promoted molybdenum carbide catalysts," Applied Catalysis, 75 (1991) pp. 267-280.

Lee, J.S; Kim, S; Kim, Y.G.; "Electronic and geometric effects of alkali promoters in CO hydrogenation over K/MO2C catalysts," Topics in Catalysis 2 (1995) pp. 127-140.

Lee, J.S.; Oyama, S.T; Boudart, M; "Molybdenum Carbide Catalists I. Synthesis of Unsupported Powders," Journal of Catalysis 106, (1987), pp. 125-133.

Lee, J.S; Volpe, L; Ribeiro, F.H; Boudart, M; "Molybdenum carbide Catalysis II. Topotactic Synthesis of Unsupported Powders," Journal of Catalysis 112, (1988), pp. 44-53.

Ozkan, U; Schrader, G.L; "NiMoO4 Selective Oxidation Catalysts Containing Excess MoO3 for the Conversion of C4 Hydrocarbons to Maleic Anhydride," Journal of Catalysis 95, (1985), pp. 120-136.

Taylor, C.E; Shamsi, A; Anderson, R.B; Ladner, K; Lyons, D; Velsoki, G; OST Technical Progress Report—Teamwork Plan FY 1998 Results.

International Application No. PCT/US2007/010342, Search Report dated Oct. 17, 2007.

International Application No. PCT/US2007/010342, Written Opinion dated Oct. 17, 2007.

International Application No. PCT/US2007/010342, International Preliminary Report on Patentability dated Oct. 8, 2008.

Parallel Australian Patent Application No. 2007243242; Notice of Acceptance dated Jan. 21, 2011.

* cited by examiner

*Primary Examiner* — Jafar Parsa
(74) *Attorney, Agent, or Firm* — Santangelo Law Offices, PC

(57) ABSTRACT

At least one embodiment of the inventive technology focuses on a new composition that comprises hexagonally close packed molybdenum carbide crystals, in addition to metallic nickel crystals and/or sodium, and having use as a catalyst in a Fischer-Tropsch process to produce alcohol. At least one embodiment of a related aspect of the inventive technology is a Fischer-Tropsch reaction to produce alcohols from carbon monoxide and hydrogen using the aforementioned composition to catalyze reactions producing higher alcohols.

32 Claims, 13 Drawing Sheets

PROCESS AND CATALYST FOR PRODUCTION OF MIXED ALCOHOLS FROM SYNTHESIS GAS

CROSS-REFERENCES TO RELATED APPLICATIONS

This is the United States National Phase of international patent application No. PCT/US2007/010342, Filed 27 Apr. 2007, which claims priority to and benefit of U.S. Provisional Application 60/796,068, filed 27 April, 2006, each of said applications hereby incorporated herein by reference.

GOVERNMENT RIGHTS

This application relates to work performed under US DOE Cooperative Agreement DE-FC26-98FT40322. The US government may have certain rights in this inventive technology, including "march-in" rights, as provided for by the terms of US DOE Cooperative Agreement DE-FC26-98FT40322.

TECHNICAL FIELD

This inventive technology relates generally to a new composition, and new process that uses the composition to produce mixed alcohols. More specifically, different embodiments of the inventive technology focus on a new catalyst usable in a Fischer-Tropsch process, and a Fischer-Tropsch process that uses the new catalyst to produce alcohol, preferably with a high selectivity towards ethanol over methanol.

BACKGROUND

The Fischer-Tropsch (F-T) process for making alcohols dates to the 1920s. Work in this field up to the late 1970s was reviewed by Anderson, et. al. (R. B. Anderson, J. Feldman and H. H. Storch, *Ind. Eng. Chem.*, 44 (1952), 2418; R. B. Anderson, *Catal. Rev.*, 21 (1980) 53). The F-T process involves passing synthesis gas (or syngas, a mixture of carbon monoxide and hydrogen) over a catalyst to form alcohols. The Anderson papers list a number of catalysts for making alcohols in this way, including those containing zinc, copper, chromium, manganese, thorium and iron. Many times these are promoted with alkali metal salts.

Syngas is made by gasifying carbon-containing materials (such as coal, plant or animal-based biomass, petroleum-based hydrocarbons, natural gas or municipal solid waste) according to the following general equation:

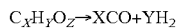

$$C_xH_yO_z \rightarrow XCO + YH_2$$

where $X \geq 1$; $Y \geq 0$, $Z \geq 0$. This reaction is carried out under high heat conditions. If the starting material is rich in carbon (such as coal or coke) oxygen or steam are used as reactants. In order to get the correct ratio of hydrogen ($H_2$) to carbon monoxide (CO) the water gas shift reaction is usually employed:

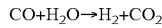

$$CO + H_2O \rightarrow H_2 + CO_2$$

The optimum $H_2$/CO ratio depends on the catalyst and temperature employed and the products desired. This reaction is usually carried out in a separate reactor with catalysts other than the F-T types.

In the 1980s, Dow discovered that molybdenum sulfide was preferred versus the previous art. The advantages include: (1) The high water-gas shift activity allowed the use of carbon monoxide-rich syngas without installing a separate water-gas shift reactor. (2) High yields and selectivities for higher alcohols were realized. The $MoS_2$ catalyst required alkali promoters and a cobalt co-catalyst to obtain the best results. (G. J. Quarderer and G. A. Cochran, "Process for producing alcohols from synthesis gas", U.S. Pat. No. 4,749,724 (Jun. 7, 1988); R. R. Stevens and M. M. Conway, "Mixed alcohols production from syngas", U.S. Pat. No. 4,752,623 (Jun. 21, 1988); R. R. Stevens and M. M. Conway, "Mixed alcohols production from syngas", U.S. Pat. No. 4,831,060 (May 16, 1989); R. R. Stevens, "Process for producing alcohols from synthesis gas", U.S. Pat. No. 4,882,360 (Nov. 21, 1989)). Typical temperatures and pressures were 250 to 330° C. and 1500 psig. The Dow patents disclosed that alkali-promoted molybdenum carbide is a catalyst for alcohol production but gave no examples and stated that $MoS_2$ is the most preferred catalyst. The Dow patents also disclosed the use of nickel as a co-catalyst but gave no examples with $Mo_2C$.

Most recently, Lee and co-workers (H. C. Woo, K. Y. Park, Y. G. Kim, I-S Nam, J. S. Chung and J. S. Lee, *Applied Catalysis*, 75 (1991), 267; J. S. Lee, S. Kim and Y. G. Kim, *Topics in Catalysis*, 2 (1995), 127) have used alkali promoted, high surface area molybdenum carbides to produce higher alcohols from syngas at about 300° C. and pressures as low as 145 psig. Two practical methods have been described for synthesizing high surface area $Mo_2C$. One involves a Temperature Programmed Reduction (TPR) of a metal salt with a fluid stream. (J. S. Lee, S. T. Oyama, M. Boudart, *Journal of Catalysis*, 106 (1987), 125) The other requires the reaction of a vaporized metal salt with a solid substrate. (M-J Ledoux, J-L Guille, C. Pham-Huu and S. Marin, "Production of heavy metal carbides of high specific surface area", U.S. Pat. No. 5,308,597 (May 3, 1994). M-J Ledoux, J-L Guille, C. Pham-Huu and S. Marin, "Production of heavy metal carbides of high specific surface area", U.S. Pat. No. 5,391,524 (Feb. 21, 1995).) Boudart, et. al. (J. S. Lee, S. T. Oyama, M. Boudart, *Journal of Catalysis*, 106 (1987), 125; J. S. Lee, L. Volpe, F. H. Ribeiro, M. Boudart, *Journal of Catalysis*, 112 (1988), 44) were the first to disclose a procedure for producing high surface area, catalytically active $Mo_2C$. The reactants were powdered $MoO_3$ which was carburized with a methane/hydrogen or ethane/hydrogen mixture using the TPR (Temperature Programmed Reduction) procedure. TPR is a procedure for gradually deoxygenating and carburizing the $MoO_3$ powder using a programmed heating rate. The TPR parameters were determined so as to produce mainly active, crystalline $Mo_2C$ hexagonal close-packed crystals. The final temperature had to be high enough with the proper heating rate to produce active $Mo_2C$ crystals. If the final temperature was too high or the heating rate too slow at high temperatures, a non-carbidic carbon layer would cover the catalyst and deactivate it. The TPR process appears to be most easily scaled-up to production levels.

The driving force for the work by Dow Chemical and Lee, et. al. was to produce an alcohol mixture suited to blend with gasoline. It is therefore desirable that the alcohol mixture should approximate the boiling range of gasoline with minimal purification. An efficient process would have high mass yields of mixed alcohols per unit mass of catalyst with high selectivity towards $C_2$ to $C_5$ alcohols. The main variables controlled during alcohol synthesis were: temperature, pressure, space velocity and reactant gas ratio ($H_2$/CO). Space velocity (SV) reflects the rate of reactant gas going through the reactor per unit of catalyst. Herein it is expressed as liters of CO+$H_2$ per hour per kg of catalyst. Product yield is expressed as total grams of alcohol produced per hour per gram of catalyst. One measure of selectivity is grams of higher alcohols ($C_2$OH+), particularly ethanol ($C_2$OH), produced per hour per gram catalyst. When compared to total alcohol yield, this measure of selectivity expresses the selectivity towards higher molecular weight alcohols than methanol. $C_2OH+$ refers to all alcohols with molecular weights greater than methanol. Higher selectivity is more desirable because high methanol concentrations give lower boiling ranges than desirable for mixing with gasoline and can lead to engine corrosion.

It would be desirable to develop a catalyst that could produce a similar product as the $Mo_2S$, but that did not contain sulfur. With regulations for sulfur becoming more stringent, t seems reasonable that such a catalyst might be valuable because there would be no possibility of making sulfur-containing byproducts (which is a distinct possibility when using a sulfur-containing catalyst).

It would also be desirable for the yields to increase with space velocity without sacrificing selectivity towards higher alcohols. Indeed, such is a goal of at least one embodiment of the inventive technology.

DISCLOSURE OF INVENTION

The inventive technology includes, in embodiments, a unique catalyst composition, the method for making the same and the method for using this catalyst to convert synthesis gas to alcohols. The catalyst comprises primarily molybdenum carbide ($Mo_2C$), with Nickel (Ni) and/or Sodium (Na) present as co-catalysts. Sodium (Na) was present on the catalyst surface at concentrations of about 0 to 20 atom % but only trace amounts, if any, were ever detected in the bulk. Other than sodium, the catalyst surface was also composed of molybdenum (20 to 30 atom %), carbon (22 to 30%), nickel (0 to 8%) and oxygen (25 to 60%). The bulk composition usually included Mo, Ni and C in significant amounts with occasional traces of O, Pd and Na. The presence of sodium on the catalyst surface increased the ethanol selectivity for the $Mo_2C$ catalyst even though Ni was not present. Two crystal structures, hexagonal close-packed $Mo_2C$ and metallic Ni were detected.

Several advantages versus $MoS_2$ and $Mo_2C$ were observed when evaluating the catalysts: (1) The new compositions contained no sulfur and thus produced no sulfur-containing products. (2) They produced higher alcohol yields than $Mo_2C$ and $MoS_2$. (3) They produced alcohols with much higher ethanol to methanol selectivity than either $MoS_2$ or $Mo_2C$.

It is an object of at least one embodiment of the inventive technology to provide an efficient process that has high mass yields of mixed alcohols per unit mass of catalyst with high selectivity towards $C_2$ to $C_5$ alcohols. Higher selectivity is more desirable because high methanol concentrations give lower boiling ranges than desirable for mixing with gasoline and can lead to engine corrosion.

It is an object of at least one embodiment of the inventive technology to provide a catalyst that could produce a similar product as the $Mo_2S$, but that did not contain sulfur.

It is an object of at least one embodiment of the inventive technology to provide a Fischer Tropsch process in which yields increase with space velocity without sacrificing selectivity towards higher alcohols.

MODES FOR CARRYING OUT THE INVENTION

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Disclosure appearing below details catalyst preparation to illustrate how the novel composition (composition of matter) was made. The disclosure then describes the characterization procedures demonstrating the novelty of the composition. Additional disclosure is presented to describe the alcohol synthesis reactor and the conditions used to generate the high alcohol yields and the unusually high selectivity towards ethanol versus methanol. It is noted that the experimental details presented herein are not intended in any manner to limit the scope of the inventive technology as described in the claims.

Catalyst Preparation

A stirred quartz reactor was constructed to synthesize $Mo_2C$ from $MoO_3$ and the inventive composition of $Mo_2C$, metallic nickel and sodium (Ni/$Mo_2C$). The procedure involves carburizing and reducing a molybdenum oxide and a nickel salt with a gaseous hydrocarbon/hydrogen mixture at a programmed heating rate. Procedures described in References 9 and 10 were generally followed for preparing high surface area $Mo_2C$ catalysts. The conditions taught in these references were applicable to small catalyst yields of the order of 0.5 to 1.0 grams. We designed a new reactor to scale-up production to about 6 to 15 grams of catalyst. In order to improve uniformity in the final product at the higher production rates, we added a stirrer system. We also had to make some modifications to gas flow rate. A rotating kiln reactor may also be employed for still higher production rates.

Figure 1:
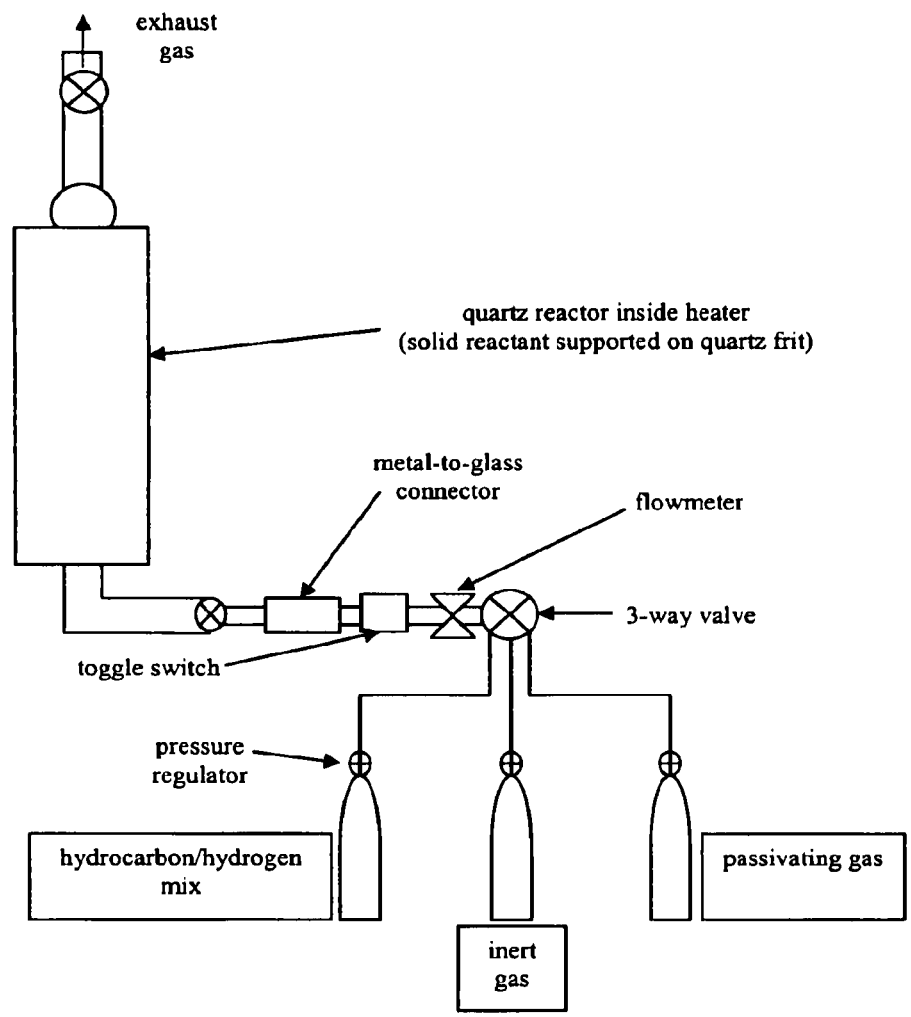
FIG. 1 shows an overall view of an embodiment of the composition (e.g., catalyst) preparation system.
Figure 2:
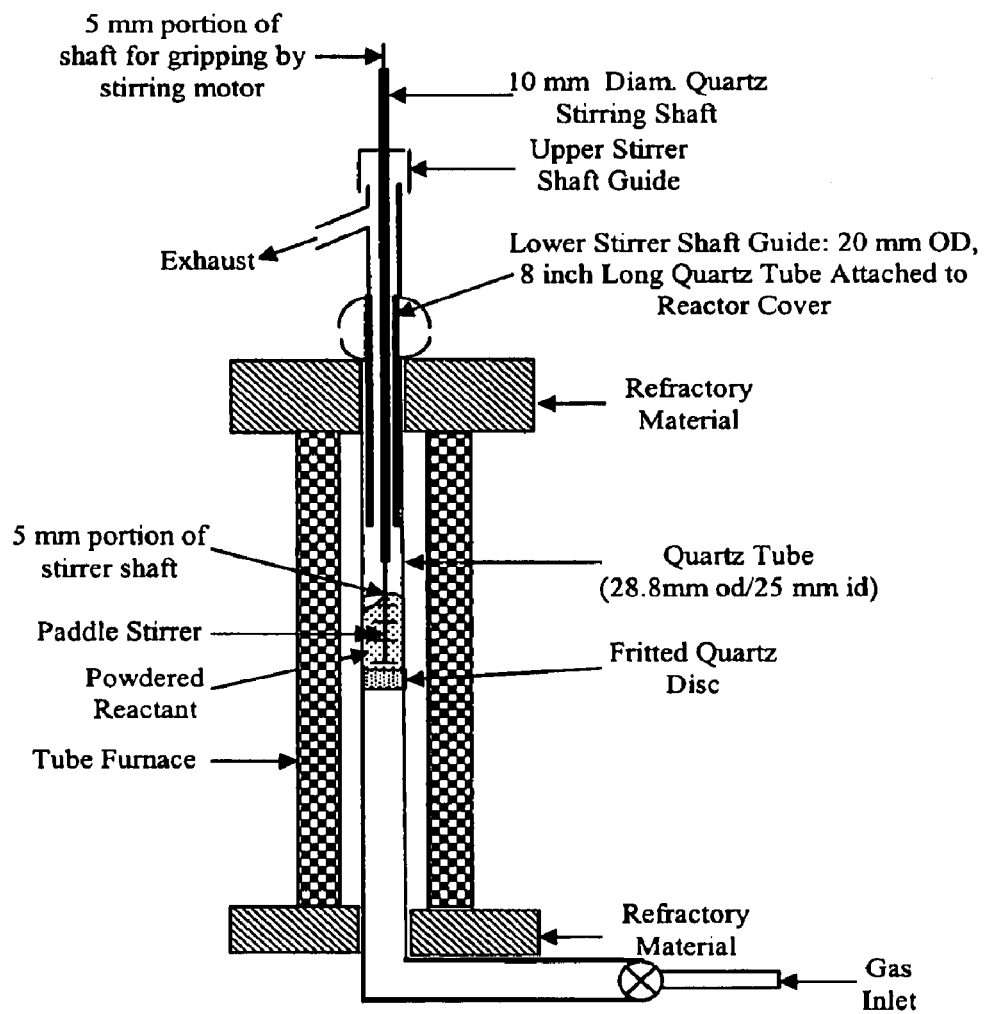
FIG. 2 shows a stirred quartz reactor as used in embodiments of the inventive technology.
Figure 3:
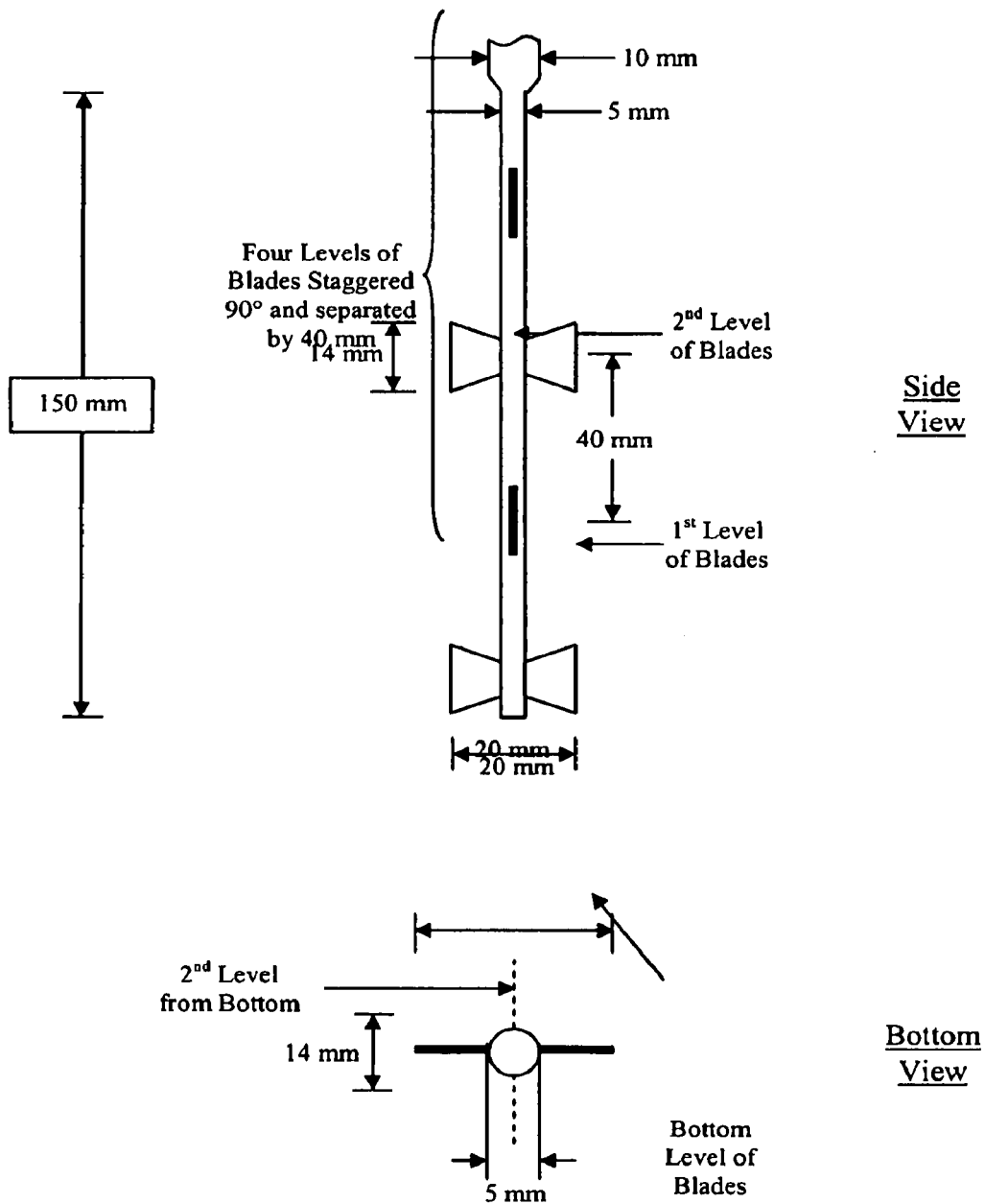
FIG. 3 shows a propeller for the stirred quartz reactor useful in at least one embodiment of the inventive technology, showing all propellers tilted at 90 degrees.

Several views of the reactor are shown in FIGS. 1-3. An overall picture of the reactor assembly is shown in FIG. 1. The body of the quartz reactor was located within an oven. Details of the quartz reactor and the quartz stirring rod are shown in FIGS. 2 and 3, respectively. Oven temperature and heating rate was carefully controlled to ±0.5° C. The temperature was continuously recorded electronically. Solid catalyst precursor powders were supported on a fritted quartz cylinder located near the center of the reactor. After loading the powder into the reactor (one manner of establishing a surface), a slow flow (200 ml/min) of argon kept the precursor powder dry and oxygen-free.

The Ni/$Mo_2C$ catalyst can be prepared from several sources of nickel. $NiMoO_4$ was the usual nickel-containing precursor. It was purchased from two sources (Alfa-Aesar and Aldrich) having widely varying concentrations of contaminants, primarily sodium. A virtually sodium-free $NiMoO_4$ can be prepared as described in Reference 13. As is shown in the subsequent examples, higher sodium levels produce catalysts with lower surface area. NiO is another nickel salt that can be used in combination with $MoO_3$ to produce a desirable catalyst. This nickel oxide compound is easier to obtain in very high purity than the molybdate.

The argon blanket was maintained until the reaction was initiated. To begin startup, the stirrer was turned on to agitate the powder and the hydrogen/hydrocarbon reactant gas blend was passed through the reactor at typically 2 l/min from a compressed gas cylinder when about 20 g of powdered precursor salts were used. In almost every case the reactant gas mixture was 10% ethane and 90% hydrogen. Higher gas flow rates would be used for scaled-up operations. Higher or lower ethane to hydrogen ratios can also be used. Other hydrocarbon gases (e.g. methane or propane) can be employed as well. The temperature program was initiated when the argon blanketing the reactor was displaced by ethane/hydrogen. The standard temperature program was initiated at ambient conditions with a temperature jump to 277° C. within about 5 minutes. From 277°, the temperature was increased to 657° C. at a rate of 0.5° C./minute. At 657°, the heater was turned off and the reactor was purged with argon overnight while cooling to ambient conditions. Alternate ramp rates, beginning and ending temperatures could also be used.

Most of the exhaust gas was vented to the outside while a small amount was monitored every 25 minutes by an SRI 8610 Gas Chromatograph. The gases monitored were: hydrogen, methane, ethane, carbon monoxide, carbon dioxide, water, oxygen and nitrogen. Initially only the reactant gases, ethane and hydrogen were detected. As the reaction proceeded with climbing temperatures, the product gases methane, carbon monoxide, carbon dioxide and water were detected.

After the reaction was completed and the temperature had cooled below about 50° C., passivation could be initiated to stabilize the catalyst surface and render it less pyrophoric. The passivation gas (1% oxygen remainder nitrogen) passed through the catalyst at 200 ml/min for two hours when the reactor was loaded with 20 g of precursor powder. Usually a 3 to 14° C. exotherm was observed during the first 10 minutes of passivation. Following passivation, argon was passed through the reactor at about 100 ml/min to blanket the catalyst.

Ni/$Mo_2C$ and $Mo_2C$ were made according to Examples 1 and 2, respectively. The same procedure, outlined above, was followed for each example 1 and 2. Only the precursor powder content was different.

Example 1

This is the standard precursor powder recipe including 10.0 grams $MoO_3$ and 10 grams $NiMoO_4$. Both materials were purchased from Alfa Aesar. The $NiMoO_4$ was 98% pure. The $MoO_3$ was ACS grade, 99.5% pure. Typical catalyst yields were about 11 to 13 grams. This is an example illustrating an aspect of the inventive technology.

Comparative Example 2

20.0 grams of $MoO_3$ was added to the reactor. Yields of 11.5 to 14 grams were obtained.

Examples 3 through 8

The source of sodium in the catalyst of Example 1 (Ni/$Mo_2C$) was the $NiMoO_4$ precursor powder from Alfa Aesar. Examples 3 through 8 illustrate the effect of sodium on catalyst effectiveness. All catalyst preparation procedures and ingredients were as described for Examples 1 and 2 except where noted.

Example 3

This is the standard precursor powder recipe used in Example 1 except that the sodium concentration in the $NiMoO_4$ was measured as 15,000 ppm by weight using Glow Discharge Mass Spectrometry and Flame Photometry. All solid precursor powders were from Alfa Aesar of the same type used in Example 1. The Ni compound was from a different lot and the sodium level was probably not the same as in Example 1.

Example 4

This recipe used 20 g of the $MoO_3$ to which was added 0.23 g $Na_2CO_3$. ACS reagent grade, primary standard $Na_2CO_3$ was used from Sigma-Aldrich (99.95 to 100.05% purity on a dry basis). This is a Na/Mo weight ratio of 0.0075.

Example 5

This is the standard precursor powder recipe used in Example 1 except that the $NiMoO_4$ was purchased from the Aldrich Chemical Company. It's sodium level was measured at 430 ppm by Glow Discharge Mass Spectrometry and Flame Photometry.

Example 6

This is the standard recipe used in Example 2 with 20 g of $MoO_3$ as the sole precursor powder.

Example 7

This recipe uses 16.58 g of the $MoO_3$ and 3.42 g of NiO. The NiO was purchased from The Aldrich Chemical Company as 99.999% pure (<10 ppm Na). The Ni/Mo weight ratio was the same as in Examples 1, 3 and 5. There were two purposes to this example: (1) An alternate source of Ni was used to determine the catalyst effectiveness and (2) This is the lowest sodium content compound containing nickel that was available.

The elemental composition, in atom %, are listed in Table 2. These results were obtained from an XPS Survey Scan.

The same alcohol synthesis reactor was used to check for catalyst efficacy with the same preparation procedures. The following reactor conditions were employed: $H_2$/CO ratio=2; SV=8740 $hr^{-1}$; pressure=1000 psig; temperature=288 to 329° C.

TABLE 2

Elemental Composition of Catalyst Surfaces for Examples 3 through 7

| Catalyst | C | Mo | O | Ni | Na |
|---|---|---|---|---|---|
| Example 3 (Ni/Mo$_2$C-high Na) | 29 | 22 | 32 | 3 | 14 |
| Example 4 (Mo$_2$C + Na) | 29 | 27 | 33 | 0 | 10 |
| Example 5 (Ni/Mo$_2$C-low Na) | 29 | 29 | 40 | 0.8 | 1.2 |
| Example 6 (Mo$_2$C) | 22 | 28 | 50 | 0 | 0 |
| Example 7 (Ni/Mo$_2$C-from NiO) | 22 | 25 | 52 | 1.3 | 0 |

Table 3 summarizes alcohol yields and selectivity for the catalysts in Examples 3 through 7. The temperature listed reflects the highest selectivity and yields for each catalyst. The catalysts of Examples 3 and 5 showed the highest selectivity towards the higher alcohols and ethanol. The "Total Alcohol Yield" was highest for all the catalysts containing nickel (Examples 3, 5 and 7). However, Example 7 (catalyst made from NiO) showed lower selectivity towards the higher alcohols than all other catalysts, including those which had no nickel (Examples 4 and 6). Comparing Examples 4 and 6, the presence of sodium on the surface of the nickel-free $Mo_2C$ in Example 4 has imparted higher selectivity towards ethanol although the yield of higher alcohols is lower than the catalyst without sodium in Example 6.

TABLE 3

Comparison of Catalyst Efficacy

| Catalyst | Temp (° C.) | Total Alcohol Yield (g/g cat-hr) | Higher Alcohol Yield (g/g cat-hr) | Ethanol/Methanol Ratio |
|---|---|---|---|---|
| Example 3 | 316 | 0.29 | 0.23 | 2.6 |
| Example 4 | 329 | 0.22 | 0.12 | 2.5 |
| Example 5 | 329 | 0.28 | 0.23 | 3.1 |
| Example 6 | 329 | 0.22 | 0.16 | 1.9 |
| Example 7 | 288 | 0.31 | 0.14 | 0.6 |

Table 4 summarizes the relationship between catalyst surface area and Na content on the catalyst surface as determined by XPS. It is clear that higher sodium levels give lower surface area materials.

TABLE 4

Effect of Sodium Concentration on Surface Area

| Catalyst | Atom % Sodium | Surface Area (m$^2$/g) |
|---|---|---|
| Example 3 | 14 | 7.7 |
| Example 4 | 10 | 6.4 |
| Example 5 | 1.2 | 25.9 |
| Example 6 | 0 | 38.9 |

Catalyst Characterization

The physical and chemical characterization data are presented to illustrate how the Ni-containing catalyst of Example 1 is different from $Mo_2C$ as well as the disclosed Ni-containing molybdenum carbide in the Dow patents.

Surface area, surface chemistry, bulk crystal structure and bulk elemental composition were determined. Four samples each of Examples 1 (Ni/Mo$_2$C) and 2 (Mo$_2$C) were characterized using each technique. The BET technique was used with nitrogen sorption data to determine the surface area. The surface elemental composition and bonding was determined using X-ray Photoelectron Spectroscopy (XPS). Bulk crystal structure was assessed using Wide-Angle X-ray Scattering (WAXS). Visual inspection of the crystals in the bulk of the catalyst was made with a Scanning Electron Microscope (SEM). The Wavelength Dispersive Spectroscopy (WDS) mode of the SEM was used to semi-quantitatively determine the elemental composition of the catalyst's bulk.

Surface Area—BET surface area was determined using nitrogen adsorption with a Micromeritics TriStar 3000 Surface Area and Porosity Analyzer. The surface area for the $Mo_2C$ samples was generally higher than that for the Ni-containing catalyst. However, the sodium content in the precursor powder was the main variable controlling surface area, as is shown in Examples 3 through 6. The range in surface area for Example 2 was 25 to 43 m$^2$/g. For Example 1 (the Ni-containing catalyst) the surface area was 4.4 to 5.5 m$^2$/g. It is unusual that the more active catalyst had much lower surface area, since higher surface area usually corresponds with higher activity. Yet, Example 1 had much higher activity for alcohol synthesis than Example 2.

XPS—XPS scans approximately the top 5 nm of a sample thus making it a chemical surface probe. Survey scans revealed the surface elemental composition as shown in Table 1. The noticeable differences between the two types of samples are: (1) Much lower oxygen levels for the Ni-containing catalyst (2) The strong presence of sodium in the Ni-containing catalyst.

TABLE 1

Elemental Composition of Catalyst Surfaces for Examples 1 and 2

| Catalyst | C | Mo | O | Ni | Na |
|---|---|---|---|---|---|
| Example 1 (Ni/Mo$_2$C) | 22-28 | 25-28 | 27-31 | 5-6 | 11-17 |
| Example 2 (Mo$_2$C) | 22-28 | 26-30 | 45-49 | 0 | 0 |

Figure 5:
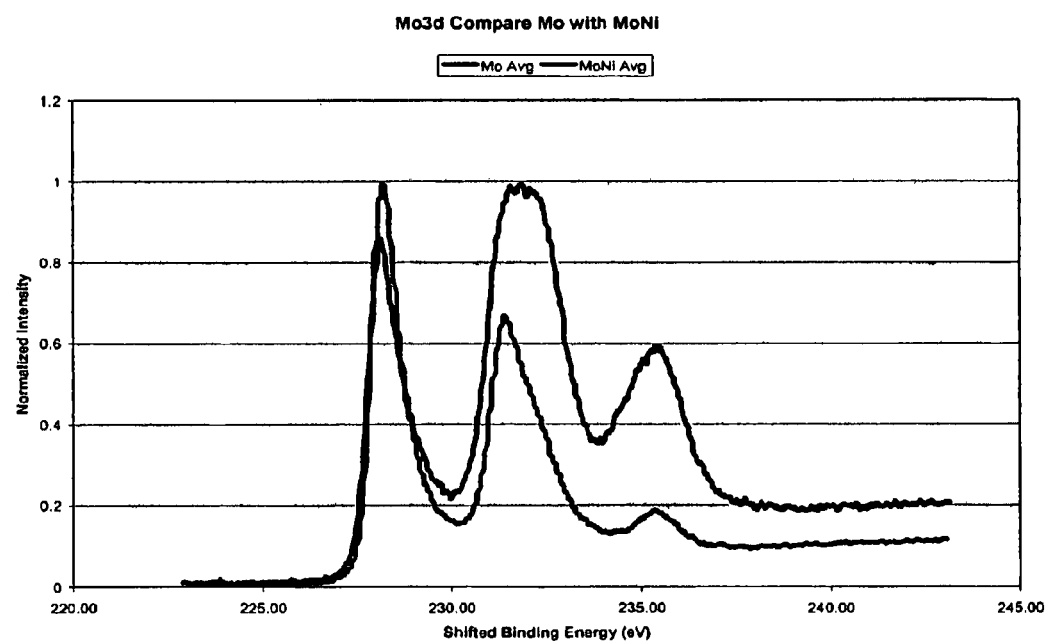
FIG. 5 shows an XPS Mo3d spectral comparison of $Mo_2C$ and MoNiC relative to at least one embodiment of the inventive composition.
Figure 6:
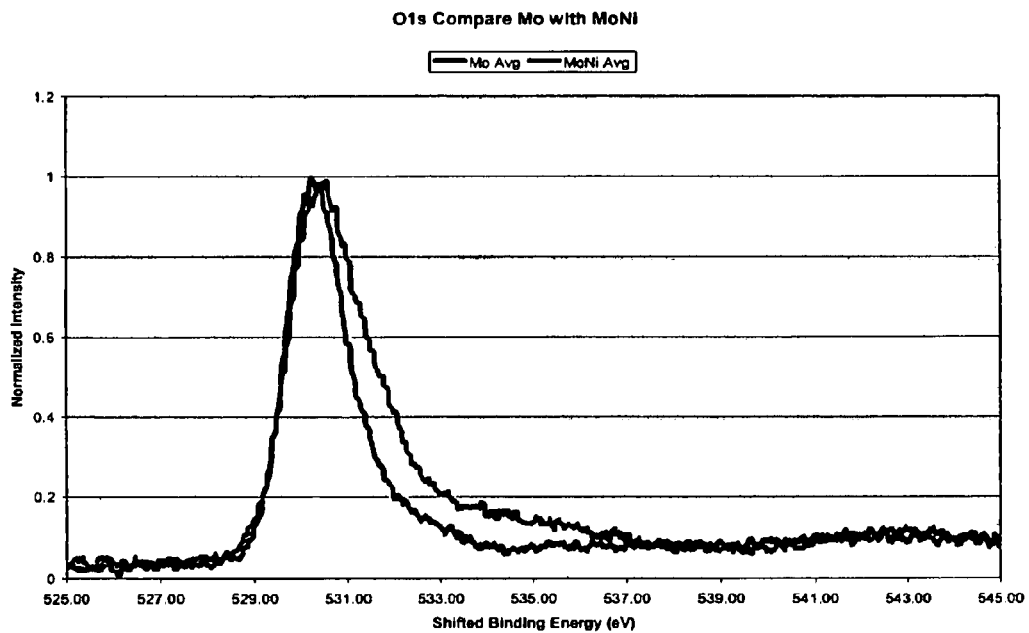
FIG. 6 shows an XPS O1s spectral comparison of $Mo_2C$ and MoNiC relative to at least one embodiment of the inventive composition.

Spectral differences were observed for the 1s electrons of carbon (C1s—FIG. 4), the 3d electrons of molybdenum (Mo3—FIG. 5) and the is electrons of oxygen (O1s—FIG. 6). Spectral assignments were made, where possible, using the following three references: (1) NIST XPS Database (http://srdata.nist.gov/xps/); (2) L. J. Gerenser, J. Vac. Sci. Technol. A8, 3682 (1990); (3) J. F. Moulder, W. E. Stickle, P. E. Sobol, K. D. Bomden, *Handbook X-ray Photoelectron Spectroscopy*, published by Physical Electronics, Inc. (1995).

Figure 4:
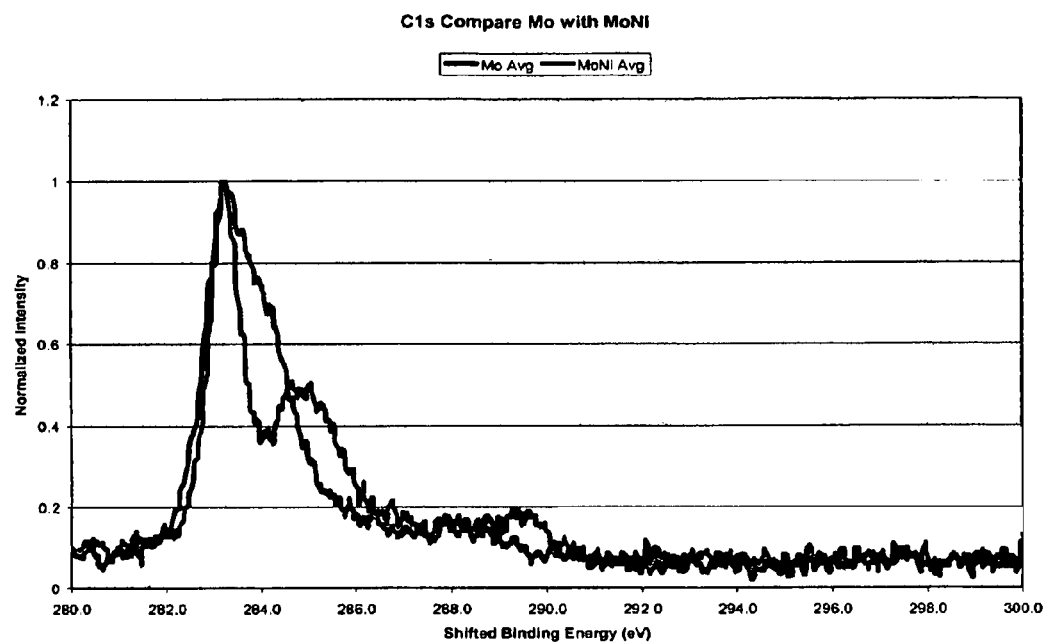
FIG. 4 shows an XPS C1s is spectral comparison of $Mo_2C$ and MoNiC relative to at least one embodiment of the inventive composition.

FIG. 4 compares averaged, normalized C1s spectra for Examples 1 (Ni/Mo$_2$C) and 2 (Mo$_2$C). The distinguishing feature of Example 2 is a skewed peak between 282 and 286 eV (electron volts). This is actually a combination of the peak at 283 eV representing Mo—C bonding and the ubiquitous, non-carbidic carbon peak at 284 eV. Example 1, however, has a very sharp peak for the carbidic bonding at 283 eV. This could be either Mo—C or Ni—C bonding. A separate broader peak at high energy values could represent a combination of the non-carbidic and an unidentified bonding with carbon, possibly Mo, Ni, C and O in an unusual combination.

The molybdenum (Mo3d) spectral differences are illustrated for both examples in FIG. 5. There are three distinct peak areas for both catalysts. The lowest energy peak is primarily the result of Mo—C bonding. The nickel-containing catalyst has a slightly higher concentration of this bond. The two higher energy peak areas are primarily due to Mo—O bonding and the Mo$_2$C catalyst has far more intensity in these areas. The higher Mo—O bonding in the Mo3d spectrum for the Mo$_2$C catalyst is in agreement with the higher concentration of oxygen found in the elemental composition of this catalyst described earlier and listed in Table 1.

A more pronounced high energy shoulder is observed for the nickel catalyst in the O1s Spectral comparison (FIG. 6). Ni—O—Mo bonding might account for this. Both Ni—O and Mo—O bonding result in similar peak positions and are difficult to separate.

Figure 7:
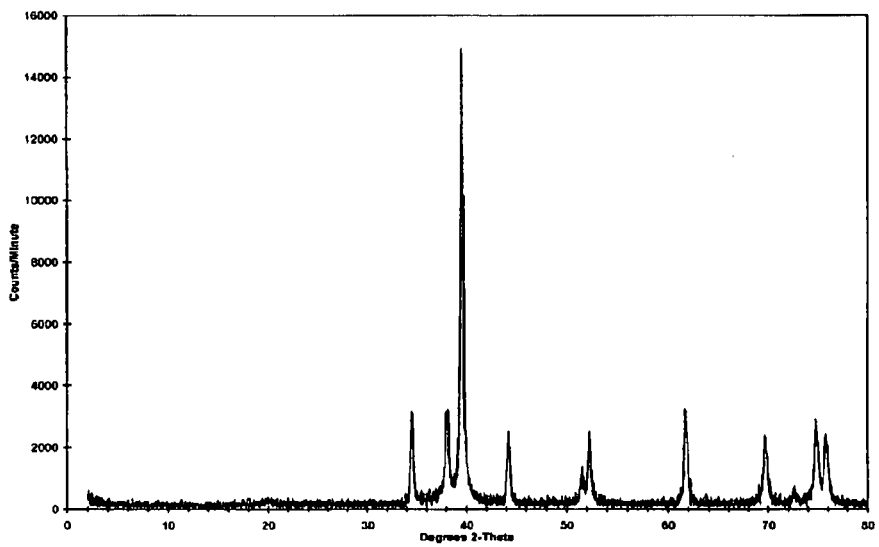
FIG. 7 shows a WAXS spectrum for NaNiMoC (example 1) relative to at least one embodiment of the inventive composition.
Figure 8:
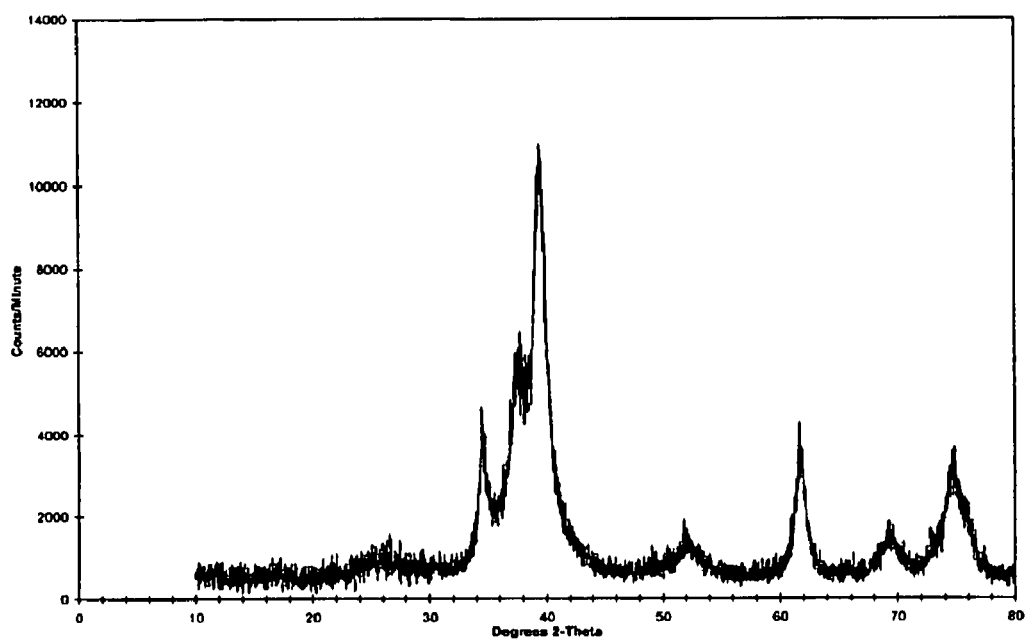
FIG. 8 shows a WAXS spectrum for $Mo_2C$ (example 2) relative to at least one embodiment of the inventive composition.

WAXS—The x-ray spectra for Examples 1 and 2 are compared in FIGS. 7 and 8, respectively. The spectrum for the sample of Example 1 (FIG. 7) clearly shows only reflections representing metallic nickel and hexagonal close-packed Mo$_2$C. Data base spectra for each crystal type have signature reflections at: 44.5 and 52.0 degrees (metallic nickel) and 34.5, 38.0, 39.5, 52.2 and 61.5 degrees (Mo$_2$C). The high intensity reflections at 44.8, 71.2 and 78.2 degrees, which are representative of Ni$_3$C, are not present.

The spectrum for Mo$_2$C (FIG. 8) shows the characteristic reflections for the hexagonal close-packed crystal structure. The reflections for this sample are much broader than for the Ni-containing catalyst. This is consistent with the higher surface area observed for the sample described in Example 2 and is due to smaller crystallites in this sample.

Figure 9:
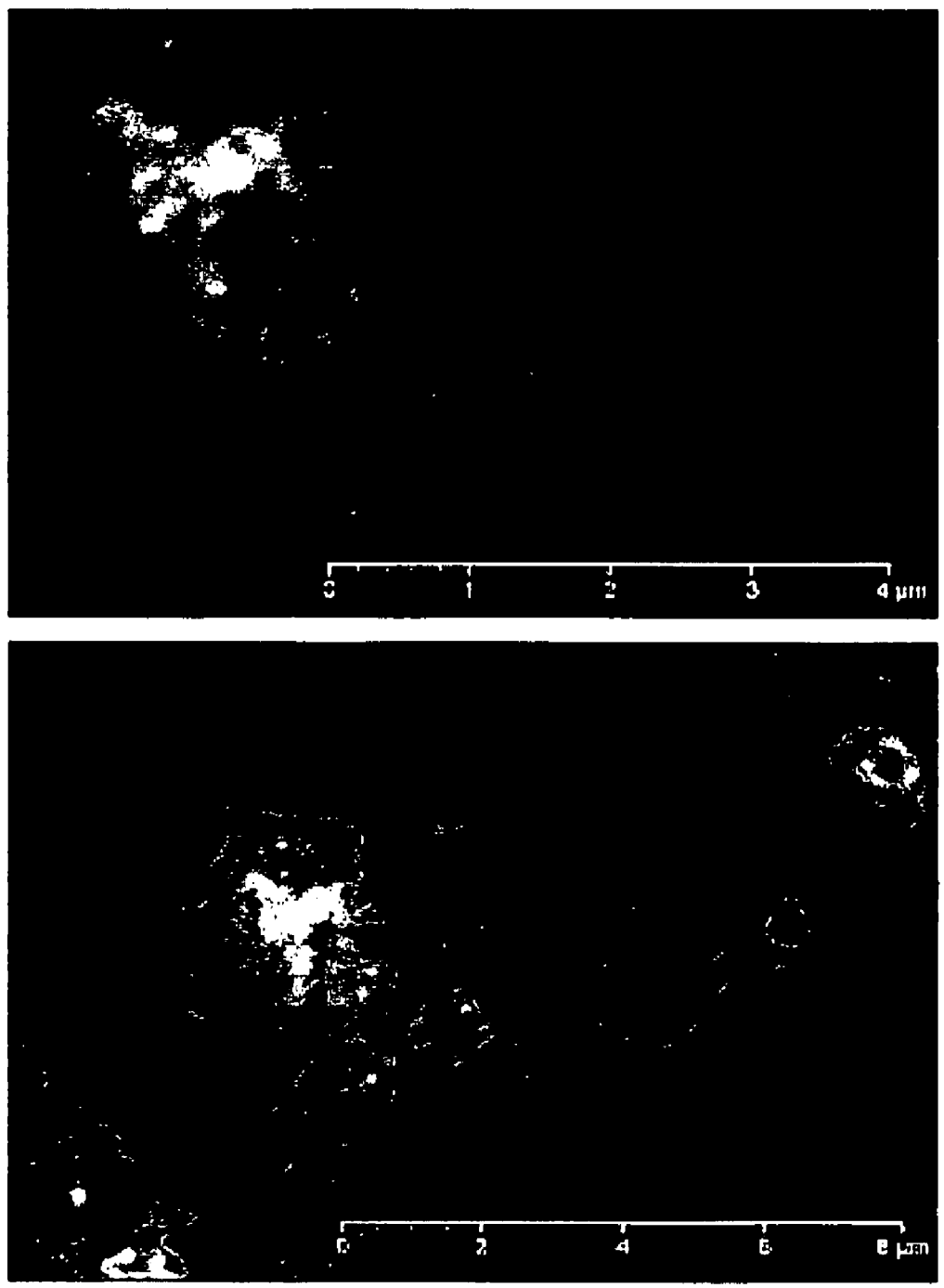
FIG. 9 shows an SEM micrograph of NaNiMoC (example 1) relative to at least one embodiment of the inventive composition.
Figure 10:
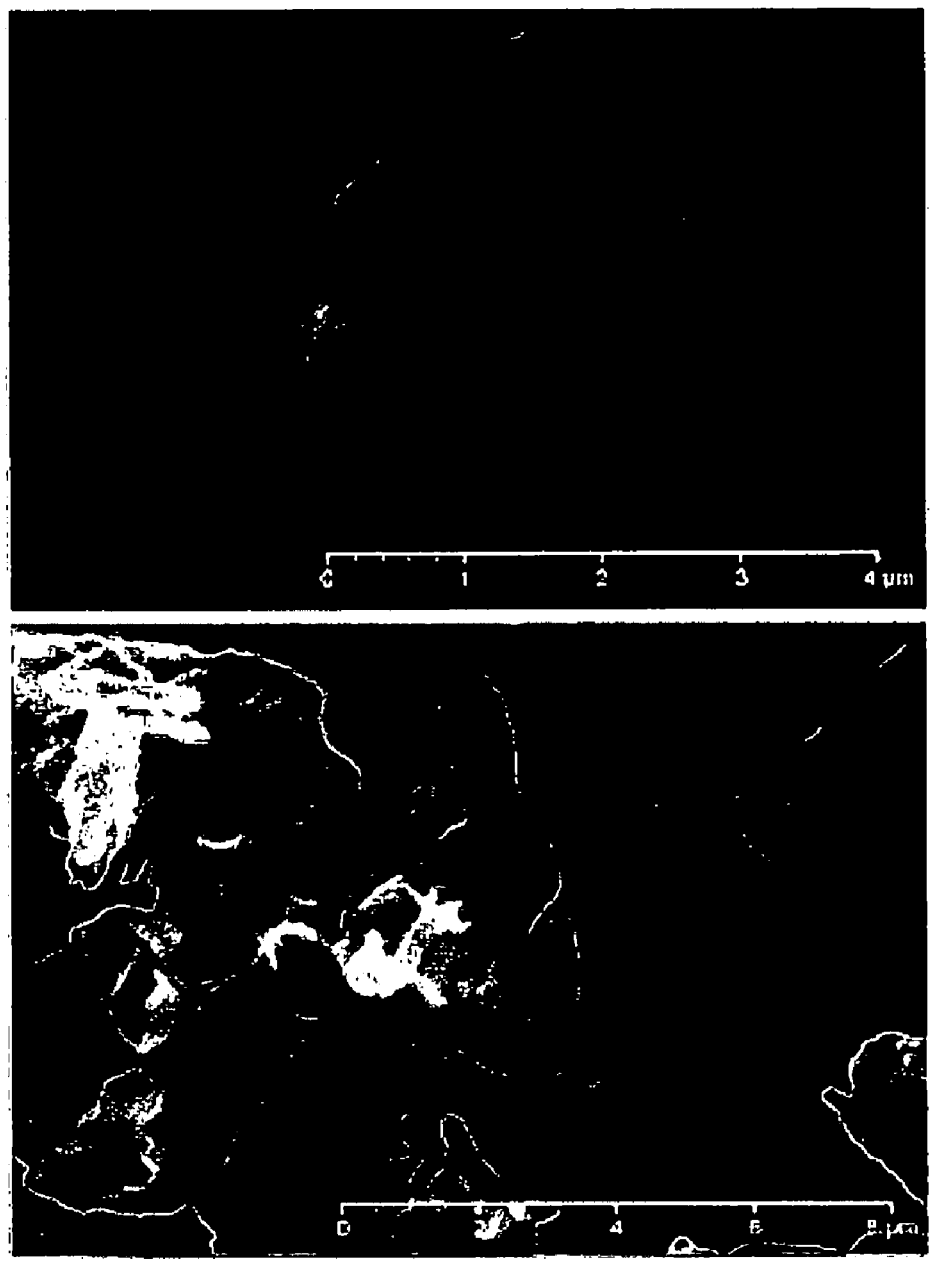
FIG. 10 shows an SEM micrograph of $Mo_2C$ (example 2) relative to at least one embodiment of the inventive composition.

SEM—The most distinguishing characteristic of the Ni-containing catalyst versus the Mo$_2$C is the presence of nodules of the order of 1 μM. To demonstrate these structural differences, representative photomicrographs of each catalyst type are shown in FIGS. 9 and 10 (for Examples 1 and 2, respectively). The carbide sample of FIG. 10 shows a platelet morphology with smoother surfaces.

WDS—WDS makes semi-quantitative measurements of the elemental composition of the bulk. The only distinction that can be made with any assurance about the composition levels of each element are those present as major, minor or trace components. The Ni-containing catalyst of Example 1 has major components of Mo, Ni and C. It also has traces of O, Pd and Na. Na is barely detectable in the bulk whereas its surface concentration is at least 10%. By contrast, the nearly pure M$_2$C of Example 2 was observed to include only Mo and C as major components with traces of S and O.

In embodiments, the inventive technology may relate to a composition (e.g., a composition of matter) having a concentration of molybdenum on a surface thereof (a composition surface) that is within the ranges of from 5 to 50 atom percentage, 10 to 4 atom percentage, and/or 20 to 30 atom percentage. In certain embodiments, the composition surface may comprise nickel in a concentration of from 0.005 to 20 atom percentage, 0.01 to 12 atom percentage, and/or from 0.5 to 8.0 atom percentage. Certain embodiments may include sodium at from 2 to 30 atom percentage, 5 to 25 atom percentage, and/or from 8 to 20 atom percentage. Of course, the term atom percentage indicates the number of atoms of the referenced element relative to the total number of atoms in the referenced component or material.

Certain aspects of the inventive technology may relate to novel manners of producing indicated compositions (whether they include molybdenum carbide and nickel material or molybdenum carbide and sodium material) usable as a catalyst in a Fischer-Tropsch process (although indeed, as mentioned, they may have other uses). It should be understood that the term molybdenum carbide and nickel material or molybdenum carbide and sodium material merely indicates that the material includes the referenced substances; other substances may be found in the material. Steps for producing a molybdenum carbide and nickel material may include: establishing a surface that comprises MoO$_3$ and a nickel salt; passing a gaseous reactant mixture over the surface; applying heat; and yielding the molybdenum carbide and nickel material. Steps for producing a molybdenum carbide and sodium material may include: establishing a surface (e.g., a composition or, more particularly in certain applications, a precursor surface) that comprises MoO$_3$ and a sodium salt; passing a gaseous reactant mixture over the surface; applying heat; and yielding the molybdenum carbide and sodium material. In either process, the gaseous reactant mixture may comprise a reducing gas (including but not limited to gaseous hydrogen) and a carburizing agent (including but not limited to a gaseous hydrocarbon such as ethane, methane, propane or butane). In those embodiments using ethane, the gaseous reactant mixture may be (as but one example), substantially 10% by volume ethane and 90% by volume gaseous hydrogen.

In catalysts prepared from, inter alia, a nickel salt, the nickel salt may include NiO, which may, potentially, have a sodium concentration of less than 10 ppm by weight (thus, it may be substantially sodium free). In particular embodiments, the nickel salt may include NiMoO$_4$, which may possibly have a sodium concentration of substantially 15,000 ppm by weight, or perhaps 430 ppm by weight, or less.

Embodiments of the process for composition production may include the step of agitating the surface (e.g., the precursor surface, such as surface that comprises MoO$_3$ and a nickel salt) via stirring materials of which the surface forms a part and/or rotating such surfaces (e.g., by rotating a reactor or a kiln). The aforementioned steps of applying heat may include heating the gaseous reactant mixture while it passes over the surface. Further, as would be understood by one of ordinary skill in the art, establishing a surface includes, e.g., establishing a supported or unsupported catalyst (or precursor, as the case may be), as would be well known to one skilled in the art.

In certain embodiments, particularly those relative to composition production, an established surface may comprise Mo and Ni in a Mo to Ni molar ratio of from 3.0 to 0.5, 2.0 to 1.0, and/or 1.75 to 1.25. The step of passing a gaseous reactant mixture over the surface may comprise the step of passing a gaseous reactant mixture having a hydrogen to carbon atom ratio of from 2 to 38, from 4 to 20 and/or from 6 to 10. In cases where the surface is a surface of a solid precursor, the step of passing a gaseous reactant mixture thereover may comprise passing a gaseous reactant mixture over the surface at from 5 to 40 SLM per mole of Mo of the solid precursor, 8 to 25 SLM per mole of Mo of the solid precursor, and/or 10 to 18 SLM per mole of Mo of the solid precursor. Further, in particular embodiments, establishing a surface that comprises $MoO_3$ and a nickel salt may itself include the step of establishing a surface that comprises $MoO_3$ and a nickel salt in a reactor. It is of note that the step of establishing a surface that comprises $MoO_3$ and a nickel salt may comprise the step of establishing a surface that further comprises sodium. Such step itself may include establishing a surface that further comprises $Na_2CO_3$ or other sodium salt.

Of course, heat may, at times, at the least facilitate reaction(s) needed for composition preparation (or, indeed, alcohol production). The step of applying heat may include applying heat to increase a temperature of the gaseous reactant mixture at a rate of from 0.05 to 5.0 degrees Celsius per minute, from 0.1 to 2.5 degrees Celsius per minute and/or 0.25 to 1.0 degrees Celsius per minute. In particular embodiments, an ideal heating rate may be substantially 0.5 degrees Celsius per minute. Start temperature ranges of the gaseous reactant mixture, e.g., may be from 150 degrees C. to 290 degrees C. and/or from 270 degrees C. to 280 degrees C.; end temperatures of the gaseous reactant mixture may be from 600 degrees C. to 700 degrees C. and/or from 650 degrees C. to 660 degrees C.

Particular embodiments of the inventive technology that relate to processes for producing a molybdenum carbide and nickel material (or molybdenum carbide and sodium material) may include the steps of reducing a molybdenum oxide and salt (e.g., a nickel salt or sodium salt) with gaseous hydrogen; carburizing the molybdenum oxide and salt (again, either nickel salt or sodium salt) with a gaseous hydrocarbon; heating the molybdenum oxide, salt, gaseous hydrogen and gaseous hydrocarbon; and yielding the molybdenum carbide and nickel (or molybdenum carbide and sodium) material. The heating rate may be controlled and, indeed, in particular embodiments, is programmed heating rate. Heating rates, including start and end temperatures, may be as described elsewhere (e.g., immediately above) in the disclosure. Further, in certain embodiments, the gaseous hydrocarbon may comprise ethane, methane, propane and/or butane. It is of note that even where the intent is to produce a molybdenum carbide and nickel material, the process may include heating sodium (e.g., a sodium salt), thereby potentially increasing selectivity towards ethanol over methanol in any Fischer Tropsch processes that thereafter use the material as a catalyst to produce alcohol. In corollary fashion, processes having the objective of producing a molybdenum carbide and sodium material may further include the step of heating nickel (e.g., a nickel salt).

Alcohol Synthesis

Figure 11:
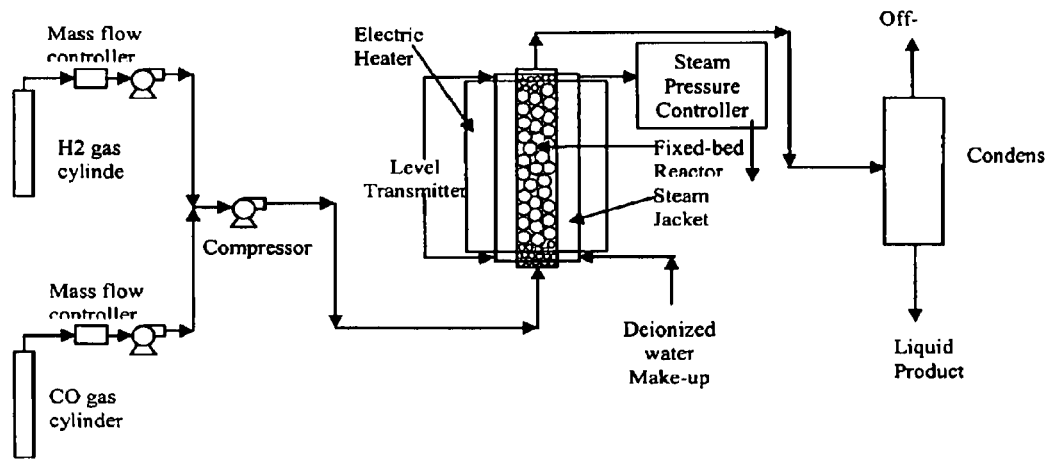
FIG. 11 shows a fixed bed alcohol synthesis reactor usable in at least one embodiment of the inventive technology.

The alcohol synthesis reactor used for testing catalyst efficacy was a fixed-bed reactor (although a slurry type reactor could be used instead) with an external steam jacket for temperature control. It was designed to operate at pressures as high as 2000 psig and temperatures of up to 325° C. Carbon monoxide and hydrogen were supplied from cylinders through mass flow controllers and entered the bottom of the reactor. Gas flow rates were controlled between 0.1 and 1.0 Standard Liters per Minute (SLM) with an uncertainty of 0.3 SLM. $H_2/CO$ ratios were about 1.0. Gas and liquid product samples were collected for analysis by gas chromatography. FIG. 11 is rough sketch illustrating the main reactor features. Slurry reactors with an inert liquid dispersing medium (e.g. high boiling hydrocarbon) may also be used.

In a typical reactor formulation, 10.3 grams of the catalyst, described above, was mixed with 2 g of $K_2CO_3$, as promoter, and 100 g of 3 mm Pyrex glass beads acting as an inert spacer. (Other inert spacer materials may be used such as carbon pellets, alumina or silica-based materials other than Pyrex glass.) The $K_2CO_3$ was first dissolved in hot water and added to 90 g of 3 mm diameter Pyrex glass beads. This mixture was then dried to put a coating of the potassium compound on the bead surface. The dried, coated beads were then powder blended with the catalyst under Argon in a glove bag.

The blend of catalyst, promoter and beads was added to the reactor under a Nitrogen blanket. The catalyst can be placed in a fixed bed or suspended in an inert hydrocarbon liquid to form a slurry which can then be contacted with carbon monoxide and hydrogen at pressures>500 psig and temperatures between 240° C. and 350° C. to form alcohols. A stainless screen was placed in the reactor so that the catalyst blend could be supported in the desired position. About 10 ml of 1 mm diameter beads was first added. Next, the 3 mm beads, promoter, catalyst blend was added followed by about 10 more grams of 3 mm beads. This was capped with about 10 ml of 1 mm diameter beads.

Alcohol yield may be defined simply as the number of grams of alcohol produced per hour per gram of catalyst. It is expressed here as either total alcohol yield (all alcohols produced from $C_1OH$, methanol, and higher) or higher alcohol yield ($C_2OH+$, all alcohols with two or more carbon atoms per molecule). Selectivity may be defined as the weight % of a particular alcohol versus total alcohol produced. As an example, a methanol selectivity of 10% means that 10% by weight of all the alcohol produced was methanol.

Figure 12:
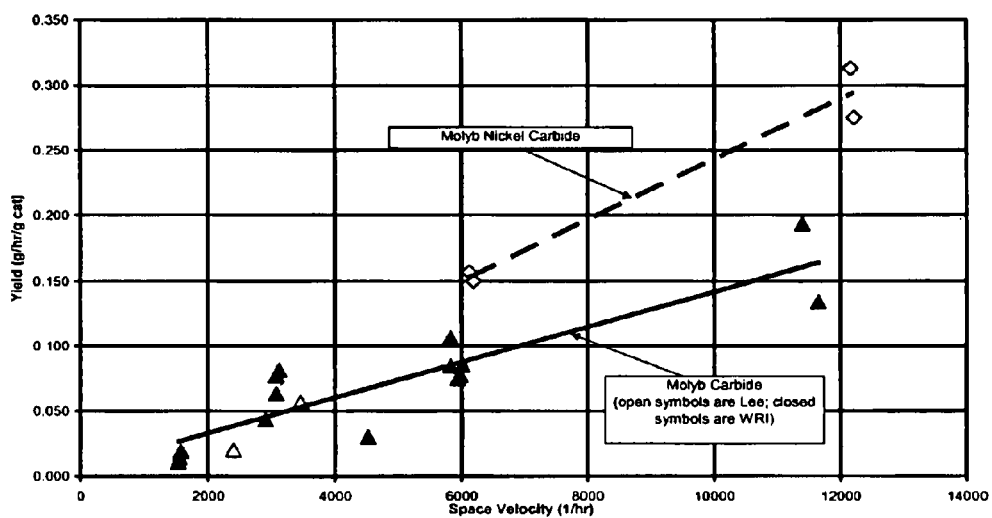
FIG. 12 shows the effect of space velocity on total alcohol yield relative to at least one embodiment of the inventive composition.
Figure 13:
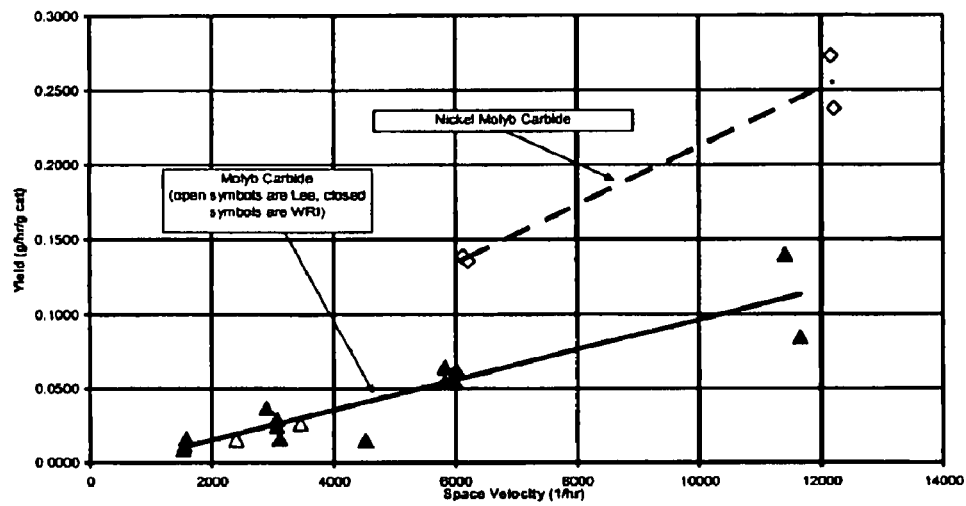
FIG. 13 shows the effect of space velocity on higher alcohol ($C_2OH+$) yield for molybdenum carbide catalysts, as relates to at least one embodiment of the inventive composition.
Figure 14:
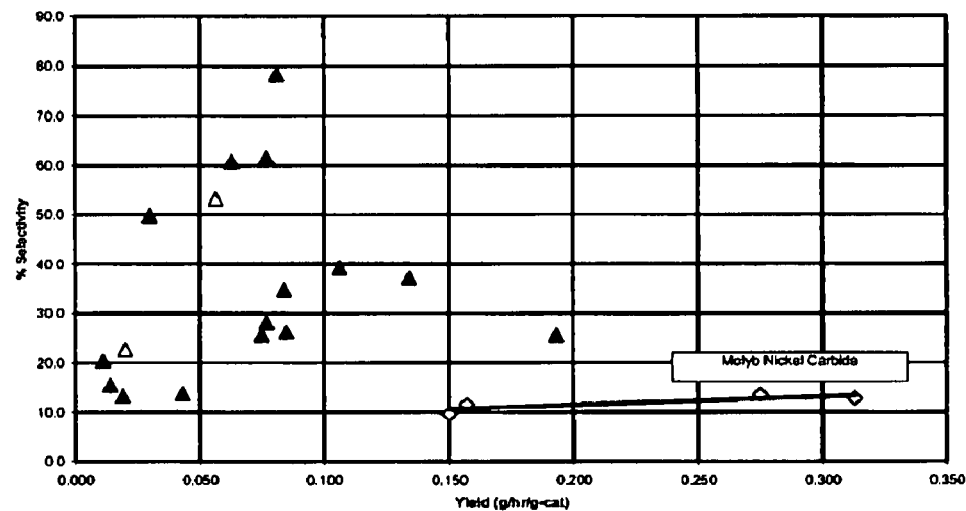
FIG. 14 shows a graph of methanol selectivity versus total alcohol yield for molybdenum carbide catalysts (filled triangles are $Mo_2C$ from Example 2; open triangles are from Lee), as relates to at least one embodiment of the inventive composition.
Figure 15:
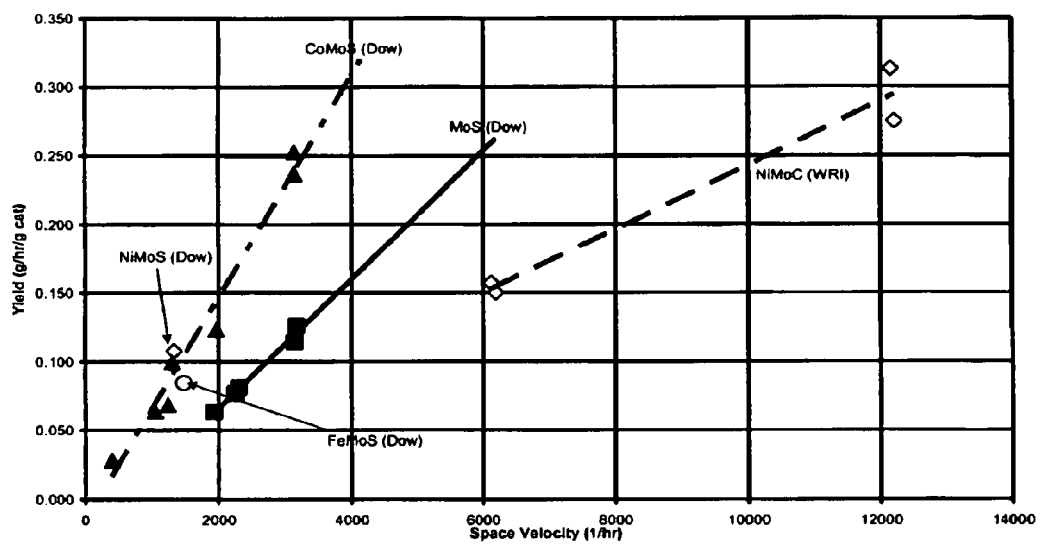
FIG. 15 shows the effect of space velocity on total alcohol yield for molybdenum carbide and sulfide catalysts, as relates to at least one embodiment of the inventive composition.
Figure 16:
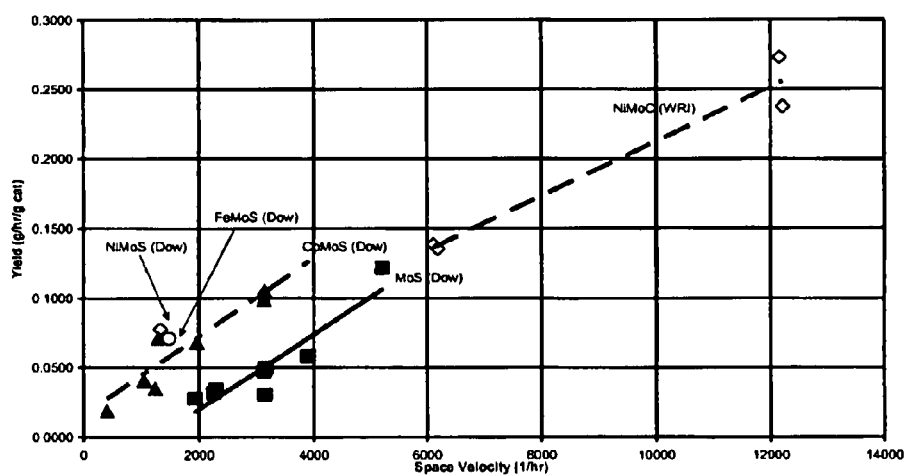
FIG. 16 shows the effect of space velocity on higher alcohol ($C_2OH+$) yield for molybdenum carbide and sulfide catalysts, as relates to at least one embodiment of the inventive composition.
Figure 17:
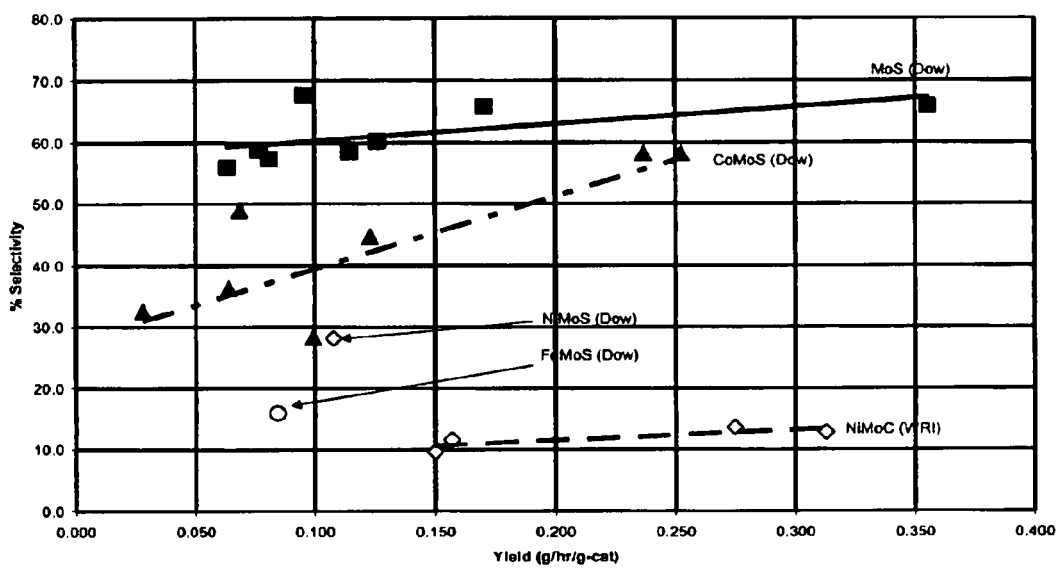
FIG. 17 shows a graph of molybdenum selectivity versus total alcohol yield for molybdenum carbide and sulfide catalyst, as relates to at least one embodiment of the inventive composition.

The data plotted in FIGS. 12 through 18 illustrate how the catalyst of Example 1 displays superior performance compared to $Mo_2C$ without co-catalyst and surface sodium and the sulfide catalysts of Dow Chemical. FIGS. 12 through 14 show that not only does using Ni and sodium as co-catalysts increase alcohol yield but they also decrease the selectivity towards methanol. This makes a more desirable automotive fuel replacement. FIGS. 15 through 17 also show better yields and lower methanol selectivity versus the sulfide catalysts for the inventive composition of Example 1. The sulfide catalysts are considered to be current state-of-the-art for alcohol synthesis. The sulfide catalyst yield data is only shown up to a Space Velocity (SV) of about 4000 $hr^{-1}$ because at higher SV values the yield decreases.

Figure 18:
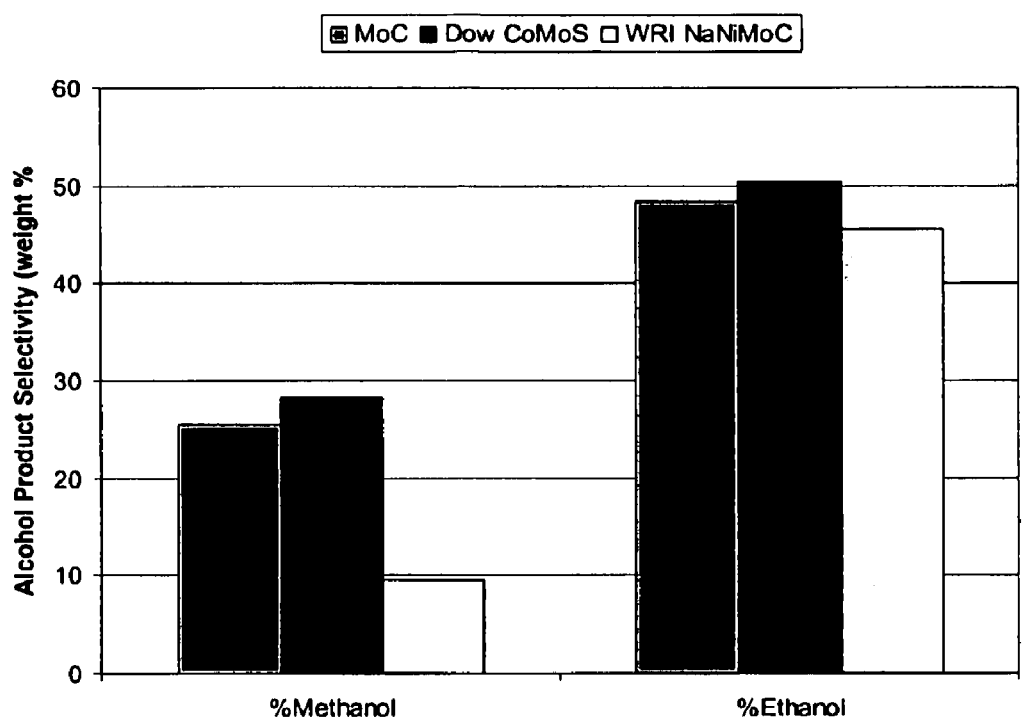
FIG. 18 shows ethanol selectivity comparisons for carbide and sulfide catalysts, as relates to at least one embodiment of the inventive technology.

In FIG. 18 the ratios of ethanol to methanol are graphed on a comparative yield basis for the catalysts of Examples 1 and 2. The ratio is almost 5:1 for the Ni-containing catalyst versus less than 2:1 for the catalyst in the comparative example 2. Also compared are the alcohol ratios for Dow's best sulfide catalyst at a much lower yield. At similar yields, the ratio is less than 1:1 for the sulfide. The ethanol:methanol ratio shown in FIG. 18 is the highest published for the Dow catalyst. It is less than 2:1 and thus far inferior to the inventive composition (e.g., inventive catalyst) described herein.

As described below and elsewhere in this disclosure, particular embodiments of the inventive technology may relate to a composition usable as a catalyst in a Fischer-Tropsch process to produce an alcohol (a term that includes alcohol mixtures such as an ethanol and methanol mixture, or pure alcohol of one type). In such embodiments, the composition may comprise crystalline $Mo_2C$ (e.g., crystalline, hexagonal close-packed $Mo_2C$) and crystalline nickel (e.g., crystalline, zero valent, metallic nickel). In certain embodiments, the composition may comprise crystalline $Mo_2C$ (e.g., crystalline, hexagonal close-packed $Mo_2C$) and sodium. Of course, any referenced composition may further include other materials; indeed, in particular embodiments, the inventive technology may relate to a composition that includes crystalline $Mo_2C$, crystalline nickel, and sodium.

As should be understood, the term Fischer-Tropsch process is a broad term that includes what might be considered by some in the art to be only Fischer-Tropsch type processes; typically, the process involves passing a syngas over a catalyst under certain pressures and temperatures to produce a product such as, but not limited to, alcohol. It is of note that simply because the inventive composition(s) may be usable as a catalyst, there may indeed be other uses for that composition.

The alcohol produced through use of this or another catalyst in a Fischer-Tropsch type process may be mixed or pure (each is considered an alcohol), and in preferred embodiments includes a fuel alcohol such as ethanol. It is of note that the process may also generate non-alcohols such as food grade wax (as but one example). In certain embodiments, the catalyst's use may result in a process that is selective towards ethanol over methanol. Further, regardless of whether the inventive composition is used in a Fischer-Tropsch type process, and whether that process involves a supported or unsupported catalyst, the composition may, most precisely, be that surface that interfaces with, e.g., syngas that passes over it. Often the composition surface is a surface of a bulk material that is of the same material as the surface (e.g., comprising crystalline $Mo_2C$ and crystalline nickel, or crystalline $Mo_2C$ and sodium), although it need not be. It is also of note that the term surface is not merely a conceptual interface with no mass; the term surface as used herein refers to a surface that is indeed of sufficient depth to have mass. It also should be pointed out that the composition surface (e.g., catalyst surface), even where it is merely a surface of a bulk material that is of the same material as the surface itself, may have a different composition than the bulk material, whether due to different percent concentrations of the same substance and/or even the appearance—or non appearance—of substances.

As mentioned, a significant aspect of the inventive technology may relate to the production of an alcohol from a syngas. In particular embodiments, the process may include the steps of establishing crystalline $Mo_2C$ and crystalline nickel in a reactor (whether in supported catalyst or unsupported catalyst fashion, and whether that reactor be fixed bed, slurry type or other); pressurizing the reactor; passing the syngas over the crystalline $Mo_2C$ and crystalline nickel; heating the crystalline $Mo_2C$, the crystalline nickel and the syngas; and producing alcohol (whether ethanol, or methanol, as but two examples). The step of establishing crystalline $Mo_2C$ and crystalline nickel in a reactor may comprise the step of establishing crystalline $Mo_2C$ in a reactor such that a concentration of molybdenum on a catalyst surface in the reactor is from 5 to 50 atom percentage, from 10 to 40 atom percentage and/or from 20 to 30 atom percentage. The step of establishing crystalline $Mo_2C$ and crystalline nickel in a reactor may comprise the step of establishing crystalline nickel in a reactor such that a concentration of nickel on a catalyst surface in the reactor is from 0.005 to 20 atom percentage, from 0.01 to 12 atom percentage and/or from 0.5 to 8.0 atom percentage. The method may further comprise the step of establishing sodium in the reactor, perhaps with the intent of increasing selectivity towards ethanol relative to, e.g., methanol. In particular embodiments, the concentration of sodium on a catalyst surface may be from 2 to 30 atom percentage, from 5 to 25 atom percentage and/or from 8 to 20 atom percentage.

The syngas may be carbon monoxide and hydrogen (as but one example) and may have a hydrogen to carbon monoxide ratio of 0.1 to 10, 0.5 to 5.0 and/or from 0.75 to 2.5. Space velocities include but are not limited to 500 to 50,000 liters of syngas per hour per kg of crystalline $Mo_2C$ and crystalline nickel 1000 to 25,000 liters of syngas per hour per kg of crystalline $Mo_2C$ and crystalline nickel and/or 2000 to 15,000 liters of syngas per hour per kg of crystalline $Mo_2C$ and crystalline nickel. Pressures within the reactor may be from 100 to 10,000 psig, from 250 to 5000 psig and/or from 500 to 3000 psig. The step of heating the crystalline $Mo_2C$, the crystalline nickel and the syngas may be accomplished merely by directly heating (e.g., as with a heater established around a reactor) one or more of the crystalline $Mo_2C$, the crystalline nickel and the syngas and relying on transfer of heat from whatever is heated directly to heat other materials (whether solid, gas or other), thereby directly heating such other materials. The step of heating may include the step of heating syngas to a temperature of 200 to 375 degrees C., 250 to 360 degrees C. and/or 275 to 340 degrees C. As mentioned elsewhere in this disclosure, in particular embodiments, crystalline nickel may be metallic and zero-valent, and the crystalline $Mo_2C$ may be crystalline, hexagonal close-packed $Mo_2C$. Further, sodium may also be established in the reactor, perhaps with the desired intent of increasing selectivity towards ethanol production, and the process may involve the use of a promoter such as $K_2CO_3$. Additionally, it is of note that inert spacers such as glass beads may be placed among the catalyst in order to facilitate gas flow.

A related aspect of the inventive technology may include a process for producing an alcohol from a syngas that comprises the steps of: establishing crystalline $Mo_2C$ and sodium in a reactor; pressurizing the reactor; passing the syngas over the crystalline $Mo_2C$ and sodium; heating the crystalline $Mo_2C$, sodium, and syngas; and producing the alcohol. In such embodiments, nickel may or may not be a component of the catalyst. Regardless, indicated atom percentages of molybdenum may be as disclosed immediately above. When the catalyst does include nickel (e.g., crystalline nickel), nickel percentages may be as disclosed immediately above; the concentration of sodium on a catalyst surface—regardless of whether nickel is also present—may be from 2 to 30 atom percentage, from 5 to 25 atom percentage and/or from 8 to 20 atom percentage. Of course, as discussed, the reactor may be fixed bed or slurry type, and the syngas may include carbon monoxide and hydrogen in ratios disclosed above. Space velocities, pressures and temperatures may, but need not be as indicated elsewhere herein.

As can be easily understood from the foregoing, the basic concepts of the present invention may be embodied in a variety of ways. It involves both composition and alcohol preparation techniques as well as devices to accomplish the appropriate preparation. In this application, the preparation techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "reactor" should be understood to encompass disclosure of the act of "reacting"—whether explicitly discussed or not—and, conversely, were there effectively disclosure of the act of "reacting", such a disclosure should be understood to encompass disclosure of a "reactor" and even a "means for reacting" Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

| DOCUMENT NO. & KIND CODE (if known) | PUB'N DATE mm-dd-yyyy | PATENTEE OR APPLICANT NAME | Reference Number |
|---|---|---|---|
| 4,749,724 | 06-07-1988 | Quarderer et al. | 3 |
| 4,752,623 | 06-21-1988 | Stevens et al. | 4 |
| 4,831,060 | 05-16-1989 | Stevens et al. | 5 |
| 4,882,360 | 11-21-1989 | Stevens | 6 |
| 5,308,597 | 05-03-1994 | Ledoux, et al. | 11 |
| 5,391,524 | 02-21-1995 | Ledoux, et al. | 12 |

OTHER DOCUMENTS (INCLUDING AUTHOR, TITLE, DATE, PERTINENT PAGES)

R. B. Anderson, J. Feldman and H. H. Storch, Ind. Eng. Chem., 44 (1952), 2418. (Reference No. 1)
R. B. Anderson, Catal. Rev., 21 (1980) 53. (Reference No. 2)
H. C. Woo, K. H. Park, Y. G. Kim, I-S Nam, J. S. Chung and J. S. Lee, Applied Catalysis, 75, (1991), 267. (Reference No. 7)
J. S. Lee, S. Kim and Y. G. Kim, Topics in Catalysis, 2 (1995), 127. (Reference 8)
J. S. Lee, S. T. Oyama, M. Boudart, Journal of Catalysis, 106 (1987), 125. (Reference 9)
J. S. Lee, L. Volpe, F. H. Ribeiro, M. Boudart, Journal of Catalysis, 112 (1988), 44 (Reference 10)
(M-J Ledoux, J-L Guille, C. Pham-Huu and S. Marin, "Production of heavy metal carbides of high specific surface area", U.S. Pat. No. 5,308,597 (May 3, 1994). (Reference 11)
M-J Ledoux, J-L Guille, C. Pham-Huu and S. Marin, "Production of heavy metal carbides of high specific surface area", U.S. Pat. No. 5,391,524 (Feb. 21, 1995). (Reference 12)
U. Ozykan, G. L. Schrader, Journal of Catalysis, 95 (1985), 120. (Reference 13)

Thus, the applicant(s) should be understood to have support to claim and make a statement of invention to at least: i) each of the compositions as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

In addition and as to computer aspects and each aspect amenable to programming or other electronic automation, the applicant(s) should be understood to have support to claim and make a statement of invention to at least: xvi) processes performed with the aid of or on a computer as described throughout the above discussion, xv) a programmable apparatus as described throughout the above discussion, xvi) a computer readable memory encoded with data to direct a computer comprising means or elements which function as described throughout the above discussion, xvii) a computer configured as herein disclosed and described, xviii) individual or combined subroutines and programs as herein disclosed and described, xix) the related methods disclosed and described, xx) similar, equivalent, and even implicit variations of each of these systems and methods, xxi) those alternative designs which accomplish each of the functions shown as are disclosed and described, xxii) those alternative designs and methods which accomplish each of the functions shown as are implicit to accomplish that which is disclosed and described, xxiii) each feature, component, and step shown as separate and independent inventions, and xxiv) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A process for producing an alcohol from a syngas comprising the steps of:
    establishing a catalyst comprising crystalline $Mo_2C$ and crystalline nickel in a reactor;
    pressurizing said reactor;
    passing said syngas over said catalyst;
    heating said catalyst and said syngas; and
    producing said alcohol.

2. A process for producing an alcohol from a syngas as described in claim 1 wherein said step of establishing said catalyst in a reactor comprises the step of establishing crystalline $Mo_2C$ in a reactor such that a concentration of molybdenum on a catalyst surface in said reactor is from 5 to 50 atom percentage.

3. A process for producing an alcohol from a syngas as described in claim 2 wherein said step of establishing said catalyst in a reactor comprises the step of establishing crystalline $Mo_2C$ in a reactor such that a concentration of molybdenum on said catalyst surface in said reactor is from 10 to 40 atom percentage.

4. A process for producing an alcohol from a syngas as described in claim 3 wherein said step of establishing said catalyst in a reactor comprises the step of establishing crystalline $Mo_2C$ in a reactor such that a concentration of molybdenum on said catalyst surface in said reactor is from 20 to 30 atom percentage.

5. A process for producing an alcohol from a syngas as described in claim 1 wherein said step of establishing said catalyst in a reactor comprises the step of establishing crystalline nickel in a reactor such that a concentration of nickel on a catalyst surface in said reactor is from 0.005 to 20 atom percentage.

6. A process for producing an alcohol from a syngas as described in claim 5 wherein said step of establishing said catalyst in a reactor comprises the step of establishing crystalline nickel in a reactor such that a concentration of nickel on said catalyst surface in said reactor is from 0.01 to 12 atom percentage.

7. A process for producing an alcohol from a syngas as described in claim 6 wherein said step of establishing said catalyst in a reactor comprises the step of establishing crystalline nickel in a reactor such that a concentration of nickel on said catalyst surface in said reactor is from 0.5 to 8.0 atom percentage.

8. A process for producing an alcohol from a syngas as described in claim 1 further comprising the step of establishing sodium in said reactor.

9. A process for producing an alcohol from a syngas as described in claim 8 wherein said step of establishing sodium in said reactor comprises the step of establishing sodium in said reactor such that a concentration of sodium on a catalyst surface in said reactor is 10 to 20 atom percentage.

10. A process for producing an alcohol from a syngas as described in claim 1 wherein said step of establishing said catalyst in a reactor comprises the step of establishing crystalline $Mo_2C$ and crystalline nickel in a fixed bed reactor.

11. A process for producing an alcohol from a syngas as described in claim 1 wherein said step of establishing said catalyst in a reactor comprises the step of establishing crystalline $Mo_2C$ and crystalline nickel in a slurry type reactor.

12. A process for producing an alcohol from a syngas as described in claim 1 wherein said step of passing said syngas over said catalyst comprises the step of passing carbon monoxide and hydrogen over said catalyst.

13. A process for producing an alcohol from a syngas as described in claim 1 wherein said step of producing said alcohol comprises the step of producing ethanol.

14. A process for producing an alcohol from a syngas as described in claim 1 wherein said step of passing said syngas over said catalyst comprises the step of passing a syngas having a hydrogen to carbon monoxide ratio of 0.1 to 10.

15. A process for producing an alcohol from a syngas as described in claim 14 wherein said step of passing said syngas over said catalyst comprises the step of passing a syngas having a hydrogen to carbon monoxide ratio of 0.5 to 5.0.

16. A process for producing an alcohol from a syngas as described in claim 15 wherein said step of passing said syngas over said catalyst comprises the step of passing a syngas having a hydrogen to carbon monoxide ratio of 0.75 to 2.5.

17. A process for producing an alcohol from a syngas as described in claim 1 wherein said step of passing said syngas over said catalyst comprises the step of passing said syngas over said catalyst at a space velocity of 500 to 50,000 liters of syngas per hour per kg of crystalline $Mo_2C$ and crystalline nickel.

18. A process for producing an alcohol from a syngas as described in claim 17 wherein said step of passing said syngas over said catalyst comprises the step of passing said syngas over said catalyst at a space velocity of 1000 to 25,000 liters of syngas per hour per kg of crystalline $Mo_2C$ and crystalline nickel.

19. A process for producing an alcohol from a syngas as described in claim 18 wherein said step of passing said syngas over said catalyst comprises the step of passing said syngas over said catalyst at a space velocity of 2000 to 15,000 liters of syngas per hour per kg of crystalline $Mo_2C$ and crystalline nickel.

20. A process for producing an alcohol from a syngas as described in claim 1 wherein said step of pressurizing said reactor comprises the step of pressurizing said reactor at from 100 to 10,000 psig.

21. A process for producing an alcohol from a syngas as described in claim 20 wherein said step of pressurizing said reactor comprises the step of pressurizing said reactor at from 250 to 5000 psig.

22. A process for producing an alcohol from a syngas as described in claim 21 wherein said step of pressurizing said reactor comprises the step of pressurizing said reactor at from 500 to 3000 psig.

23. A process for producing an alcohol from a syngas as described in claim 1 wherein said step of heating comprises the step of heating said syngas to a temperature of 200 to 375 degrees Celsius.

24. A process for producing an alcohol from a syngas as described in claim 23 wherein said step of heating comprises the step of heating said syngas to a temperature of 250 to 360 degrees Celsius.

25. A process for producing an alcohol from a syngas as described in claim 24 wherein said step of heating comprises the step of heating said syngas to a temperature of 275 to 340 degrees Celsius.

26. A process for producing an alcohol from a syngas as described in claim 1 wherein said crystalline nickel comprises metallic nickel.

27. A process for producing an alcohol from a syngas as described in claim 1 wherein said crystalline nickel comprises zero valent nickel.

28. A process for producing an alcohol from a syngas as described in claim 1 wherein said crystalline nickel comprises crystalline, metallic, zero-valent nickel.

29. A process for producing an alcohol from a syngas as described in claim 1 further comprising the step of establishing sodium in said reactor.

30. A process for producing an alcohol from a syngas as described in claim 1 further comprising the step of establishing a promoter in said reactor.

31. A process for producing an alcohol from a syngas as described in claim 30 wherein said promoter comprises $K_2CO_3$.

32. A process for producing an alcohol from a syngas as described in claim 30 further comprising the step of establishing an inert spacer in said reactor.

* * * * *